(12) United States Patent
Beardsley

(10) Patent No.: US 8,236,323 B2
(45) Date of Patent: Aug. 7, 2012

(54) METHOD TO TREAT INFLAMMATION

(75) Inventor: Terry Raymond Beardsley, Temecula, CA (US)

(73) Assignee: S-Cell Biosciences, Inc., Murrieta, CA (US)

( * ) Notice: Subject to any disclaimer, the term of this patent is extended or adjusted under 35 U.S.C. 154(b) by 0 days.

(21) Appl. No.: 12/527,368

(22) PCT Filed: Feb. 13, 2008

(86) PCT No.: PCT/US2008/053891
§ 371 (c)(1),
(2), (4) Date: Dec. 18, 2009

(87) PCT Pub. No.: WO2008/101037
PCT Pub. Date: Aug. 21, 2008

(65) Prior Publication Data
US 2010/0144629 A1 Jun. 10, 2010

Related U.S. Application Data

(60) Provisional application No. 60/901,525, filed on Feb. 14, 2007.

(51) Int. Cl.
*A61K 38/16* (2006.01)
*A61K 35/12* (2006.01)
*A61K 38/00* (2006.01)

(52) U.S. Cl. ........ 424/198.1; 514/1.1; 514/886; 424/572
(58) Field of Classification Search ........................ None
See application file for complete search history.

(56) References Cited

U.S. PATENT DOCUMENTS

| | | | | |
|---|---|---|---|---|
| 5,616,554 | A | * | 4/1997 | Beardsley ..................... 514/8 |
| 6,086,898 | A | * | 7/2000 | DeKruyff et al. .......... 424/275.1 |
| 7,101,851 | B2 | * | 9/2006 | Lowman et al. ............. 514/20.6 |
| 7,196,060 | B2 | * | 3/2007 | Beardsley et al. ............... 514/8 |
| 2005/0107300 | A1 | * | 5/2005 | Beardsley et al. .............. 514/12 |
| 2007/0087968 | A1 | | 4/2007 | Beardsley | |

OTHER PUBLICATIONS

Adib-Conquy et al., International Immunology (1999) 11(5):689-98.
Beardsley et al., PNAS USA (1983) 80:6005.
International Search Report for PCT/US2008/053891, mailed on Jun. 25, 2008, 1 page.
International Preliminary Report on Patentability for PCT/US2008/053891, issued on Aug. 19, 2009, 5 pages.
Kambayashi et al., J. Immunol. (2000) 165(9):4964-69.

* cited by examiner

*Primary Examiner* — Christine J Saoud
*Assistant Examiner* — Jegatheesan Seharaseyon
(74) *Attorney, Agent, or Firm* — Morrison & Foerster LLP

(57) ABSTRACT

The present invention relates generally to the fields of pharmacology, and particularly to a method for treating inflammation, particularly inflammation of the respiratory system. The invention provides a method to reduce or ameliorate inflammation, by administering an effective amount of a protein factor originally isolated from thymic tissue, and referred to as T4 immune stimulating factor (TISF).

11 Claims, 12 Drawing Sheets

Mean Sum of Symptom Scores Post-Infection
Report

Sum of Symptom Score

| Treatment Group | Mean | Median | N | Std. Deviation |
|---|---|---|---|---|
| Test Article | .3750 | .0000 | 8 | .51755 |
| Negative Control | .8571 | 1.0000 | 7 | .69007 |
| Total | .6000 | 1.0000 | 15 | .63246 |

Mean Maximum Log-Transformed Total Leukocyte Count/ml in Nasal Wash Samples Post-Infection Report Cell Count (log)

| Treatment Group | Mean | Median | N | Std. Deviation |
|---|---|---|---|---|
| Test Article | 5.7577 | 5.8875 | 8 | .41625 |
| Negative Control | 6.0804 | 6.1117 | 7 | .12794 |
| Total | 5.9083 | 6.0079 | 15 | .34845 |

*Mean Sum of Log-Transformed Total Leukocyte Counts/ml in Nasal Wash Samples Post-Infection*

Report

Cell Count (log)

| Treatment Group | Mean | N | Std. Deviation |
|---|---|---|---|
| Test Article | 5.9805 | 8 | .40663 |
| Negative Control | 6.3639 | 7 | .09914 |
| Total | 6.1594 | 15 | .35509 |

METHOD TO TREAT INFLAMMATION

CROSS-REFERENCE TO RELATED APPLICATIONS

This application is the national phase of PCT application PCT/US2008/053891 having an international filing date of Feb. 13, 2008, which claims priority from provisional application Ser. No. 60/901,525 filed Feb. 14, 2007. The entire contents of these documents are incorporated herein by this reference.

BACKGROUND OF THE INVENTION

Inflammation is a non-specific first reaction mounted by the immune system in response to a perceived injury or threat. It is an innate defensive response, distinguished from the more precisely tailored adaptive responses of the immune system. Inflammation may work cooperatively with adaptive responses of the immune system, which develop more slowly but are more precisely targeted to a harmful agent such as a chemical or pathogen that may be causing localized injury.

Inflammation may be associated with infections, but it occurs in response to virtually any type of injury or threat, including physical trauma, cold, burns from radiation, heat or corrosive materials, chemical irritants, bacterial or viral pathogens, localized oxygen deprivation (ischemia) or reperfusion (sudden reinfusion of oxygen to ischemic tissue), and others. It includes the classic symptoms of redness, heat, swelling, and pain, and may be accompanied by decreased function of the inflamed organ or tissue. It is a generalized reaction involving several effects that may tend to combat an injurious agent that may be present at the site where an injury or threat was detected, or it may tend to contain the injury or threat to its initial location, to keep it from spreading rapidly.

Adaptive immune responses, on the other hand, develop when the body is exposed to a particular harmful agent: the cellular immune system 'learns' to recognize and attack the particular harmful agent by developing cell-mediated responses. Then, if that harmful agent persists long enough or returns later, the adaptive system recognizes the harmful agent and attacks it with a very specific response directed at the harmful agent itself. Such adaptive responses take time to develop, but are usually extremely specific, while the innate responses like inflammation involve more general changes in the affected tissue, and are not specifically targeted at an agent that is causing injury. These innate reactions involve recruitment of protective cells and substances to the area of the injury, and, unlike the adaptive responses, they typically occur rapidly.

Many methods to treat inflammation are known; however, all of them have limitations, and there are many causes of inflammation. Therefore, there is a need for new methods to combat inflammation associated with a variety of causes. The present invention provides such a method, using a protein factor known as T-4 immune stimulating factor (TISF).

TISF is a protein factor discovered from thymic tissue. It is about 50 kDa in size, with an isoelectric point of 6.5, and may be glycosylated. Its protein sequence has not been determined, but methods for its isolation and purification are disclosed in U.S. Pat. No. 5,616,554, to Beardsley, et al.

TISF has been reported to promote certain adaptive immune responses, even in subjects having a compromised immune system; thus TISF is known to be useful to treat certain types of infections that can be attacked by the adaptive immune system mechanisms. U.S. Pat. No. 5,616,554, for example, describes exposing subjects to influenza virus either with or without simultaneous treatment with TISF. The subjects were tested a few weeks later to evaluate their secondary cytotoxic killer cell response against influenza virus-infected cells, as a way to measure the effect of TISF on their cell-mediated immune (CMI) responses to the virus. Lymphocytes from subjects who had received TISF exhibited a 9-fold increase in killing activity relative to lymphocytes from control subjects, as measured by lysis of the target cells. TISF was also shown to increase antibody titers to hemagglutinin antigen (HA) in a mouse model. Thus subjects treated with TISF developed enhanced adaptive immune responses to influenza virus. This effect reduced the duration and/or severity of viral infections in animal models; however, there was no report of any direct effect on inflammation.

Subsequently, TISF has been shown to promote hematopoiesis, by stimulating the production or development of certain types of blood cells. Published U.S. Patent Application US2005-0107300. TISF has also been shown to be useful to treat certain T-Cell disorders, such as cutaneous T-cell lymphoma, by inducing apoptosis in aberrant lymphocytes. U.S. patent application Ser. No. 11/529,937, filed on Sep. 29, 2006, entitled "Methods to Treat T-Cell Disorders Using TISF", to Beardsley. These effects of TISF are useful for treating certain types of disorders, but none of these effects discloses or suggests a direct or general means to treat inflammation.

Now, surprisingly, it has now been found that TISF directly reduces inflammation. The effect develops too rapidly to result from the stimulation of adaptive immune responses that was previously reported. It resulted in reduction in the severity of inflammation and associated disease effects within the first few days following treatment.

Anti-inflammatory activity was observed in ferrets exposed to influenza virus, and the effects were documented during days 1-4 post treatment. The ferret influenza model was selected as a recognized model that closely mimics human influenza infection with regard to both the sensitivity to infection and clinical response to treatment. The test was designed to further investigate the known effects of TISF for enhancing immune responses and promoting hematopoiesis, while also watching for other possible effects. Thus the general health, blood cell counts, and other parameters were monitored for the treated subjects, and viral load was also monitored. Unexpectedly, TISF was shown to reduce the general effects of the viral infection almost immediately, and it reduced the numbers of leukocytes (neutrophils) in nasal washes of treated ferrets. These nasal washes serve as a measure of upper respiratory inflammation in the treated animals. The effects of TISF on this parameter and on other indices of health status were noticeable within the first few days following treatment with TISF.

Inflammation is regulated by the levels of various cytokines, and it has become increasingly apparent that the effects of cytokines are influenced by a variety of factors and may thus be difficult to fully understand. For example, IL-10 is generally considered immunosuppressive and/or anti-inflammatory. However, IL-10 in combination with lipopolysaccharides can promote production of TNF, IL-6 and IL-1ra in certain blood cells. J. Adib-Conquy, et al., *International Immunology*, 11(5), 689-98 (1999). TNF is a pro-inflammatory cytokine, so the stimulation of TNF would be expected to have the opposite effect and to counteract the primary effects of IL-10 alone. This may explain why IL-10 appears to exhibit pro-inflammatory effects in some situations, while inhibiting inflammatory responses in others.

Without limiting the present invention by any theory of its operation, it is believed that TISF may combat inflammation at least in part by influencing the production of certain cytokines or of certain combinations of cytokines. It has been shown that TISF can stimulate production of certain cytokines, including IL-10, BM-CSF and IL-12, under conditions where it did not significantly affect the level of TNF-α. Thus the anti-inflammatory effect of TISF may result from its effects on levels of these and other cytokines.

BRIEF SUMMARY OF THE INVENTION

T-4 immune stimulating factor ("TISF") has been shown to provide immune-boosting activity, apparently due to its ability to stimulate IL-2 production in tissue where IL-2 may have direct effects on the production or development of CMI responses. See U.S. Pat. No. 5,616,554. The molecule is described in the foregoing patent as a 50 KDa protein with an isoelectric point of 6.5. It has also been demonstrated to promote hematopoiesis, possibly by stimulating CD4+ lymphocytes. Surprisingly, it has now been found to have a direct effect on inflammation that is distinguished from its effects on the adaptive immune response or on hematopoiesis.

This demonstrates that TISF, in addition to stimulating an adaptive immune response, also directly reduces inflammation, which is a seemingly opposite effect, a suppression of an innate protective response. Unlike its effects that promote adaptive responses, when used to treat inflammation, TISF counteracts or reduces a localized 'overreaction' of the innate immune system. It acts in injured or threatened tissues, apparently reducing the accumulation of blood and non-specific cellular components (granulocytes, macrophage components) that promote healing but also produce the pain, swelling, heat and redness of inflammation. The direct effect on inflammation develops much more rapidly than a cell-mediated immune response (CMI) would be expected to develop, demonstrating that the effect on inflammation is not merely an indirect effect of treating an associated infection.

In one aspect, the present invention provides a method to treat inflammation in a subject in need of such treatment. The method comprises administering to a subject in need of treatment for inflammation, such as a subject diagnosed as having inflammation in a specific locus, an amount of TISF that is effective to reduce, treat or ameliorate the inflammation. Thus TISF is useful to treat a subject having inflammation from any etiology, and it is beneficial to administer it to subjects who would not be expected to benefit from the known CMI effects of TISF, such as subjects who have already developed symptoms of cold or flu, for example, who would not be expected to benefit from the CMI effects of TISF because those effects would develop too slowly to ameliorate the existing inflammation.

"Treat inflammation" as used herein refers to reducing at least one of the classic symptoms of inflammation, including redness, pain, swelling and heat in the affected area. Preferably, at least two of these symptoms are reduced in severity or duration by the treatment. More preferably, at least two of these symptoms are reduced within 24 hours following the treatment.

In one embodiment, the present invention provides a method to treat inflammation of the subject's respiratory system. In some such embodiments, the inflammation is inflammation of the upper respiratory system, including the mucosa of the nasal passages. This inflammation may be the result of exposure to harmful chemicals or heat, or it may result from an existing infection caused by a virus or bacterium or other pathogen.

In another embodiment, the present invention provides a method to treat inflammation by administering an effective amount of TISF by injection to a subject in need of such treatment, or administering to such subject an effective amount of TISF by topical application to a localized area of inflammation. In some such embodiments, the dosage of TISF is administered as an injectable solution. In other such embodiments, the dosage of TISF is administered topically to epidermal tissue exhibiting signs of inflammation. In some such embodiments, TISF is administered to a subject having inflammation of the upper respiratory system, in which subjects TISF may be administered by injection or via inhalation.

In another aspect, the invention provides a method to treat inflammation of the respiratory system that results from an immunological disorder such as allergy or allergic rhinitis ("hay fever"). Thus TISF may be used to treat inflammation of the respiratory tract that is associated with allergy, asthma or allergic rhinitis.

In another aspect, the present invention provides a method to treat inflammation in a subject in need of such treatment, by administering an effective amount of TISF to the subject. TISF may be administered orally, topically, by inhalation, or by injection.

In some embodiments, TISF is administered at a dosage between about 0.1 microgram and 10 milligrams per kilogram of the subject's body weight.

In one aspect, the present invention provides a therapeutic protocol that comprises diagnosing a subject as having inflammation, and administering an effective amount of TISF to the subject.

In some embodiments, the subject is one having inflammation of the upper respiratory system, such as inflammation associated with asthma or allergic rhinitis, or inflammation associated with an infection such as influenza, pneumonia, or a cold. Because of the slow development of the adaptive immune responses in such subjects, this treatment with TISF is not expected to rapidly assist in combating an infection that has already developed; however, it is useful to directly reduce the associated inflammation of the respiratory tract, and it thus promotes healing and reduces the likelihood of developing a secondary infection that may be more harmful than the initial infection.

The subject for each of the above embodiments is a mammal. In preferred embodiments, the subject may be canine, bovine, or feline. Embodiments wherein the subject is human are often preferred. The TISF used for the present invention may be derived from an animal source or from a cell culture. In preferred embodiments, TISF is produced by a cell culture method such as that described in U.S. Pat. No. 5,616,554, wherein the DNA encoding the TISF originated from a mammalian source. Preferred mammalian sources for TISF are canine, bovine, feline and human, and it is often preferred to utilize TISF which is produced from DNA that came from the same species as the subject to be treated.

DETAILED DESCRIPTION OF THE INVENTION

Figure 1A:
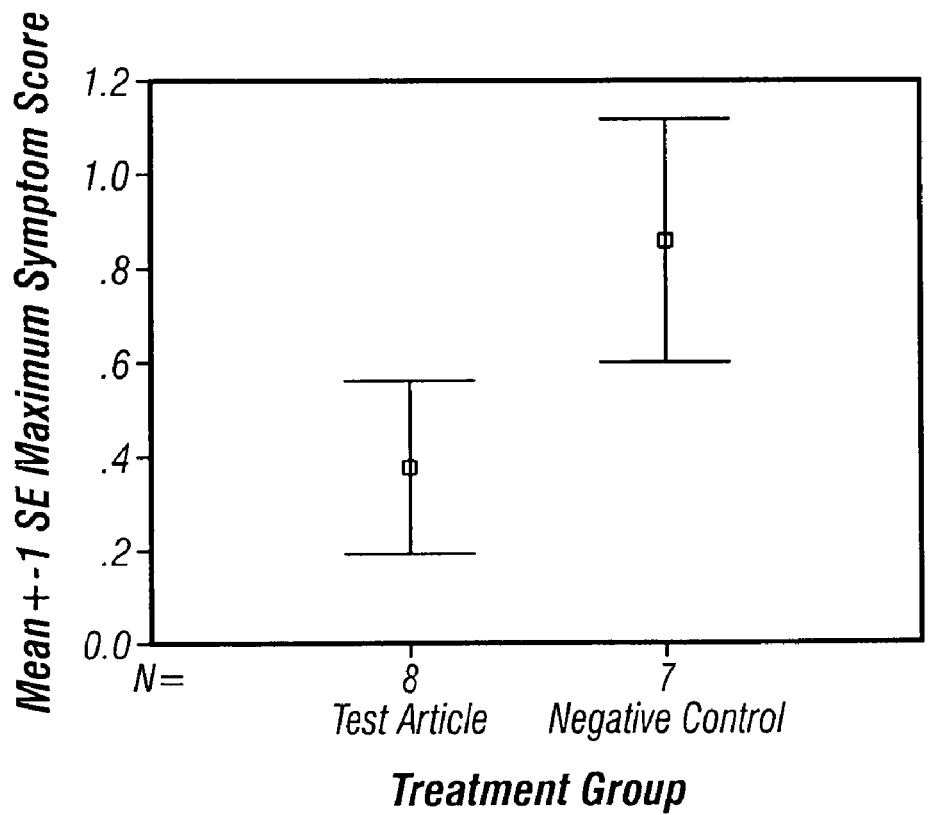
FIGS. 1A and 1B shows a summary of the maximum and overall average values for composite Symptom Scores for the TISF treated ("Test Article") and control ("Negative control") subjects for days 1-4 following treatment with TISF. The treated animals showed lower levels of overall symptomology, although the result for the small test missed the cut-off to be considered statistically significant.
Figure 1B:
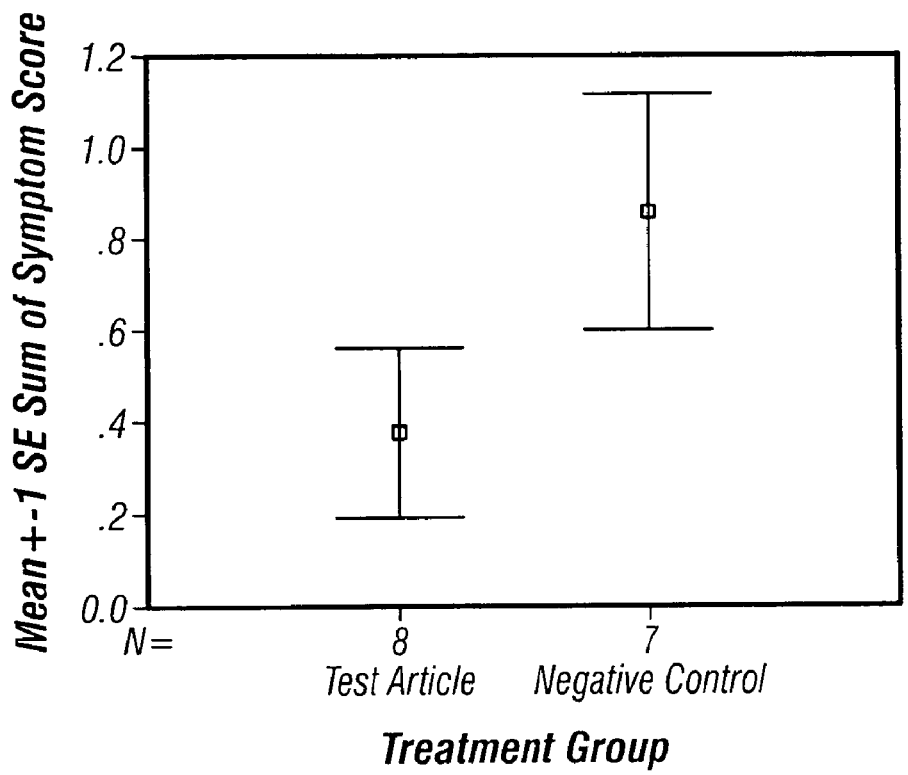

As used in the present disclosure, "inflammation" refers to the well known localized response to various types of injury or infection, which is characterized by redness, heat, swelling, and pain, and often also including dysfunction or reduced mobility. Acute inflammation, according to Cruse and Lewis, ILLUSTRATED DICTIONARY OF IMMUNOLOGY, 2d ed. (CRC Press 2003), represents "an early defense mechanism to contain in infection and prevent its spread from the initial focus. When microbes multiply in host tissues, two principal defense mechanisms mounted against them are antibodies and leukocytes. The three major events in acute inflammation are (1) dilation of capillaries to increase blood flow; (2) changes in the microvasculature structure, leading to escape of plasma and proteins and leukocytes from the circulation; and (3) leukocyte emigration from the capillaries and accumulation at the site of injury." Neutrophils escape from their endothelial location and are attracted by chemotaxis toward the site of injury. Prostaglandins and leukotrienes are formed, along with various cytokines. Non-specific defense mechanisms including natural killer (NK) cells are activated by cytokines.

By contrast, adaptive responses often take days to develop. For example, Kambayashi, et al., *J. Immunol.* 165(9), 4964-69 (2000) report that adaptive CD8+ cells expressing NK receptors develop in the lungs of influenza-infected mice beginning after about day 5 following infection (see FIG. 1: cell levels are at control level through day 5, and begin to increase thereafter to peak at about day 10). Thus adaptive responses are typically not seen during the first days following an infection.

The term "TISF" refers to a mammalian polypeptide or mixture of polypeptides of mammalian origin; the preparation of TISF and its characterization as a novel entity are described in U.S. Pat. No. 5,616,554, which is herein incorporated by reference in its entirety. TISF is alternatively referred to as EPITHYME™ and as S-Celergin at times herein and in other references. A number of factors have been described which stimulate various stages of CD4+ lymphocyte development. TISF stimulates a normally unresponsive population of cells at a later stage of the process while a factor stimulating an earlier stage of the process is described, for example, in Beardsley, et al., *PNAS* 80: 6005 (1983). TISF is thus effective as described in U.S. Pat. No. 5,616,554 for stimulation of mature T-lymphocytes, resulting in increased antiviral or antitumor activity. Herein, its effectiveness for the treatment of inflammation from any etiology, and especially inflammation of the upper respiratory tract, is disclosed.

TISF may be obtained by purification from a host animal, but is preferably obtained by purification from a cell culture by methods such as those described in U.S. Pat. No. 5,616,554, which is herein incorporated by reference in its entirety. TISF may be of feline, canine, or bovine origin; in a preferred embodiment, the TISF administered to a subject originates from the same species as that of the subject to be treated. TISF may be used to treat inflammation in canine, feline, and bovine subjects as well as in human subjects.

Administration of TISF: TISF may be administered parenterally, intraperitoneally, topically or orally. Parenteral administration is often preferred, and subcutaneous injection is sometimes preferred. For treatment of inflammation of the epidermis, topical administration may be preferred. For treatment of inflammation of the mucosa, direct application to the affected area such as by ocular application or inhalation may be preferred. Suitable methods for administration by these routes are well known in the art, and suitable formulations for each route of administration may be prepared using methods known in the art.

TISF may be admixed with one or more pharmaceutically acceptable diluents, excipients, stabilizing agents, solubilizing agents, or other pharmaceutically-indicated agents, and it may optionally be incorporated into a liposomal or slow-release matrix for administration. Suitable pharmaceutical carriers and diluents, as well as pharmaceutical necessities for their use in pharmaceutical formulations, are described in Remington's PHARMACEUTICAL SCIENCES (Alfonso Gennaro et al., eds., 17th edn., Mack Publishing Co., Easton Pa., 1985), a standard reference text in this field, in the USP/NF, and by Lachman et al. (THE THEORY & PRACTICE OF INDUSTRIAL PHARMACY, 2nd ed., Lea & Febiger, Philadelphia Pa., 1976). In the case of rectal and vaginal administration, the compositions are administered using methods and carriers standardly used in administering pharmaceutical materials to these regions. For example, suppositories, creams (e.g., cocoa butter), or jellies, as well as standard vaginal applicators, droppers, syringes, or enemas may be used, as determined to be appropriate by one skilled in the art. Parenteral, intramuscular, intraperitoneal, or other types of injection administration are often advantageous, especially since TISF may be subject to degradation if administered orally; suitable compositions for such administration are well known to those skilled in the art, and may be identified by analogy to other polypeptide pharmaceutical compositions.

The compositions of the invention may be administered by any route clinically indicated, such as by application to the surface of mucosal membranes (including: intranasal, oral, ocular, gastrointestinal, rectal, vaginal, or genito-urinary). Alternatively, parenteral (e.g., intravenous (IV), subcutaneous, intraperitoneal, or intramuscular) modes of administration may also be used. Because TISF is a polypeptide, and is thus potentially subject to degradation upon oral or topical administration, administration by parenteral (injection) methods including subcutaneous or intramuscular delivery is often preferred. To maximize its efficient utilization, subcutaneous delivery of TISF is often used, and such delivery may be concurrent with delivery of other nutrient, hydration or therapeutic agents as appropriate. For subcutaneous administration, TISF is preferably dissolved in an aqueous or isotonic solution such as saline; phosphate buffer or other conventional buffers may be added as needed to ensure stability of the composition. Further details of compositions suitable for administration of TISF are well-known to those of skill in the art by analogy to other pharmaceutical compositions which contain polypeptides as active ingredients.

The amount of TISF to be administered depends on the particular subject and indications, such as the extent, severity and duration of the inflammation as well as the status underlying cause. The mode and frequency of administration can be determined according to the desired effect, as one skilled in the art will appreciate, and the effectiveness of the chosen regimen can readily be ascertained by monitoring improvements in the symptoms of inflammation, allowing the regimen to be optimized for the particular subject being treated. In general, TISF will be administered in compositions which deliver amounts of TISF ranging between about 0.1 µg and 50 mg per kilogram of body weight of the subject. Preferred doses are generally between about 0.5 µg/kg and 10 mg/kg, and more preferably between about 1 µg/kg and 5 mg/kg. A dosage of about 1 µg/kg to 1 mg/kg is often more preferred.

Administration of TISF to a subject to be treated may be repeated as is determined to be necessary by one skilled in the art, considering the severity of the subject's inflammation and what other treatments the subject is receiving, or it may be delivered continuously to a subject via an intravenous fluid delivery system or slow-release depot device or other passive or active slow delivery means. While a single administration of TISF has been demonstrated to produce effects lasting for several days, repeated administration at intervals of a few hours to a month are contemplated and are within the scope of the invention. Thus TISF may be administered one to three times daily, or it may be administered one or two times per week, or one to two times per month. Determination of the dose required and the frequency of treatment required are within the ordinary skill in the art, since dosage and frequency can be adjusted until the desired effect is achieved. Progress is readily monitored by well-known techniques for determining the blood cell count for each type of blood cell of interest for the particular subject.

Since TISF may be used to treat inflammation associated with pathogenic infections, it is also contemplated that TISF may be admixed with or administered with other therapeutic agents suitable for treating such pathogenic infections, including but not limited to antiretroviral agents such as HIV protease inhibitors and reverse transcriptase inhibitors, radiotherapeutic treatments, and antineoplastic therapeutic agents such as alkylating agents, purine nucleoside analogs, and corticosteroids. Compositions containing a mixture of such other therapeutic agents with TISF are thus contemplated, as are treatment protocols which utilize TISF in combination with such agents.

The present invention can be better understood by way of the following examples which are representative of certain preferred embodiments thereof, but which are not to be construed as limiting the scope of the invention.

EXAMPLE 1

TISF derived from cultured bovine thymic cells was supplied as a freeze dried material and was used as a saline solution containing one microgram of protein per mL of saline solution. The subjects used were *Mustela putorius* faro, an outbred albino ferret strain. The subjects were all males, weighing about 600-1100 g on the first day of treatment, and were obtained from Highgate Farm, in England. The testing of TISF in animals was conducted by a contract laboratory familiar with procedures for testing antiviral and similar pharmaceutical candidate molecules in animal models.

Each treated ferret received 1 mL of this solution subcutaneously, delivering approximately 1 microgram of TISF per animal. Control animals received vehicle without TISF added. Prior to testing, all animals were primed with influenza A/Panama/2007/99 (H3N2) at a titre of approximately $10^{6.5}$ $TCID_{50}$/mL, which gave 100% infection of the ferrets, when 250 microliters of the virus solution was administered intranasally, 21 days before treatment with TISF or a control injection of vehicle lacking TISF.

Testing was initiated with a low pathogenic influenza strain of Avian Influenza NIBRG-14 virus (H5N1), where the external proteins of Avian Influenza A/Vietnam/1194/04 (H5N1) virus from which the polybasic HA cleavage site had been excised, and containing the internal genes of Human Influenza A/Puerto Rico/8/34 (H1N1).

The challenge virus described above at a titre of about $10^{5.25}$ $TCID_{50}$/mL using 250 microliter aliquot was administered intranasally to each ferret, providing 100% infection.

A nasal wash was performed on each animal daily following infection using a standard protocol developed by the contract laboratory. Cell counts in the nasal wash were determined using a Tryptan blue stain, as a method of determining the extent of inflammatory cell response. Blood analyses were also made at days 0, 2 and 4, and overall health and weight of the test animals were also assessed. Animals treated with TISF displayed less weight loss during the test period, and they displayed less severe clinical symptomology, although these effects were not considered statistically significant in this test. Virus shedding into the nasal wash was also evaluated, though the levels of virus were generally below detectable levels.

Figure 2:
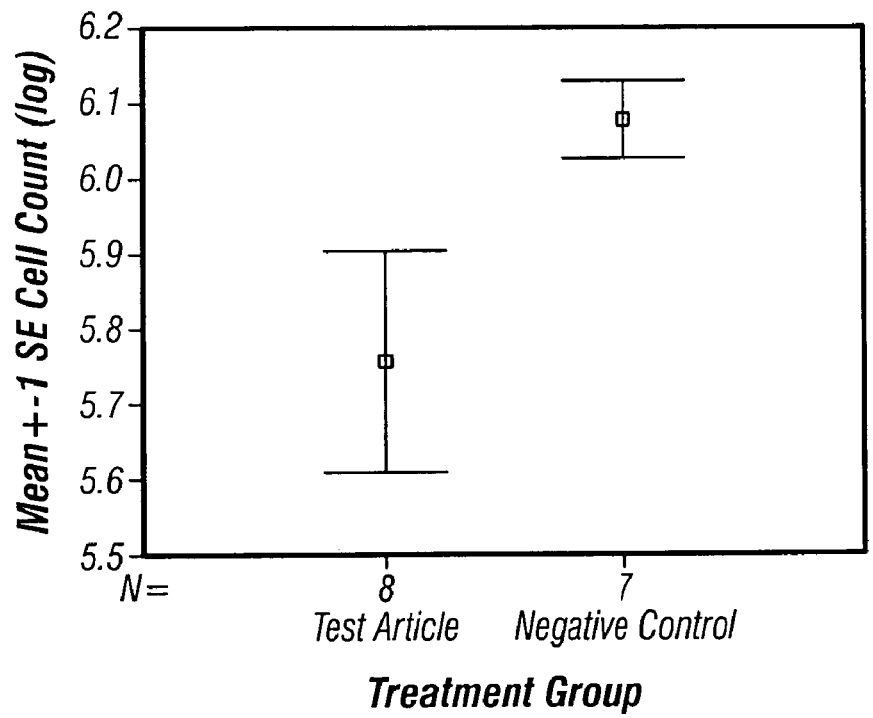
FIG. 2 shows the daily data for leukocyte counts in nasal wash samples for the TISF treated ("Test article") and control ("Negative control") subjects for days 1-4 following treatment with TISF. Even though it represents a total for days 1-4, it appears to show a significant effect in the treated animals.
Figure 3:
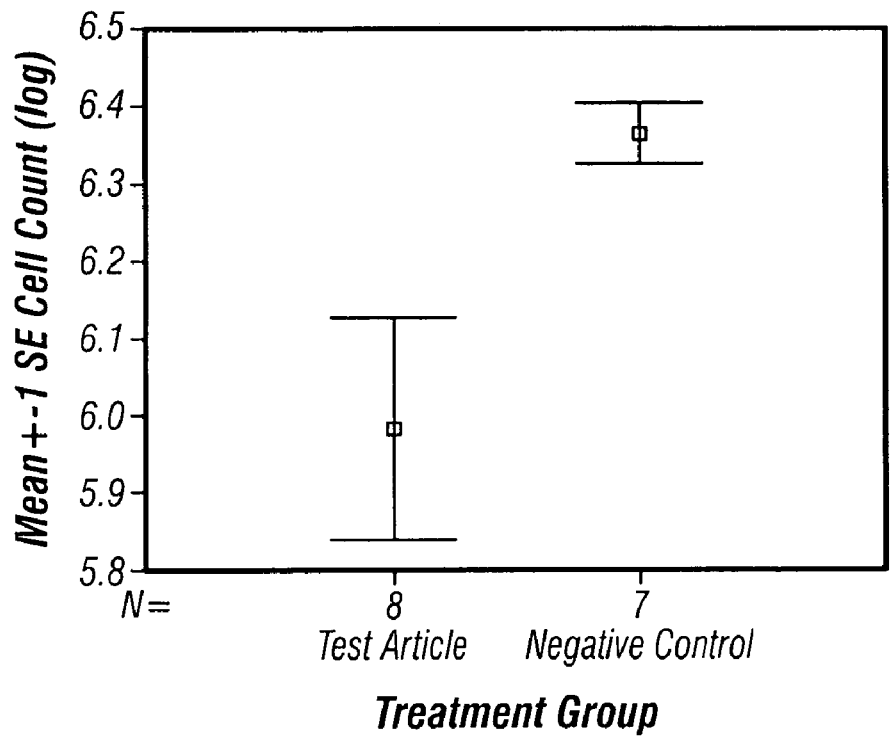
FIG. 3 summarizes the nasal wash leukocyte count data for the first four days post-treatment for the TISF treated ("Test Article") and control ("Negative control") subjects. The mean maximum value and the mean sum value (the mean sum of log-transformed total leukocyte counts) both show that TISF sharply reduced leukocyte shedding into the nasal wash samples.
Figures 1, 4A:
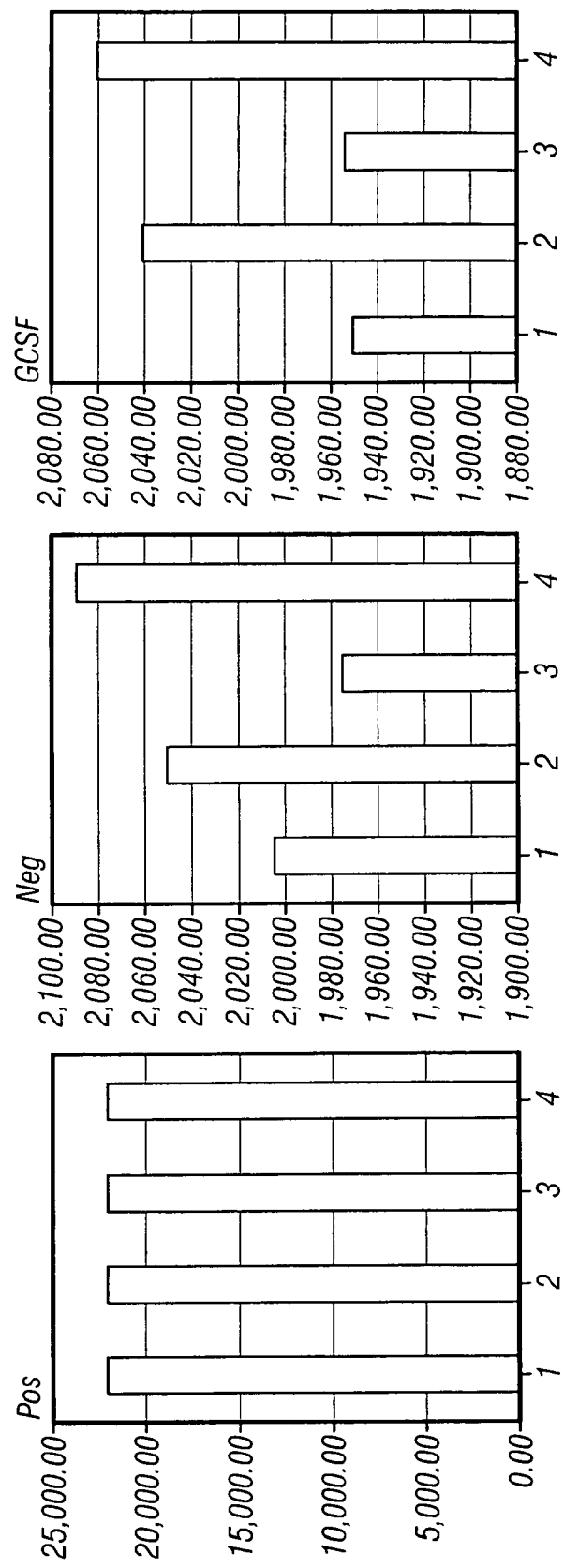
FIG. 4A through 4C shows the effect of TISF on the levels of certain cytokines, as detected by antibodies in a commercial kit for identifying cytokine levels. The antibodies used to observe cytokine levels were the RayBio® Mouse Cytokine Antibody Array from Array I and Array 1.1 from RayBiotech, Inc. Column 1 in each graph is a control sample with no TISF; columns 2, 3 and 4 correspond to samples treated with a purified sample of TISF at 1×, 0.5× and 0.25× dilutions, so that column 2 represents the highest dose of TISF.
Figures 2, 4A:
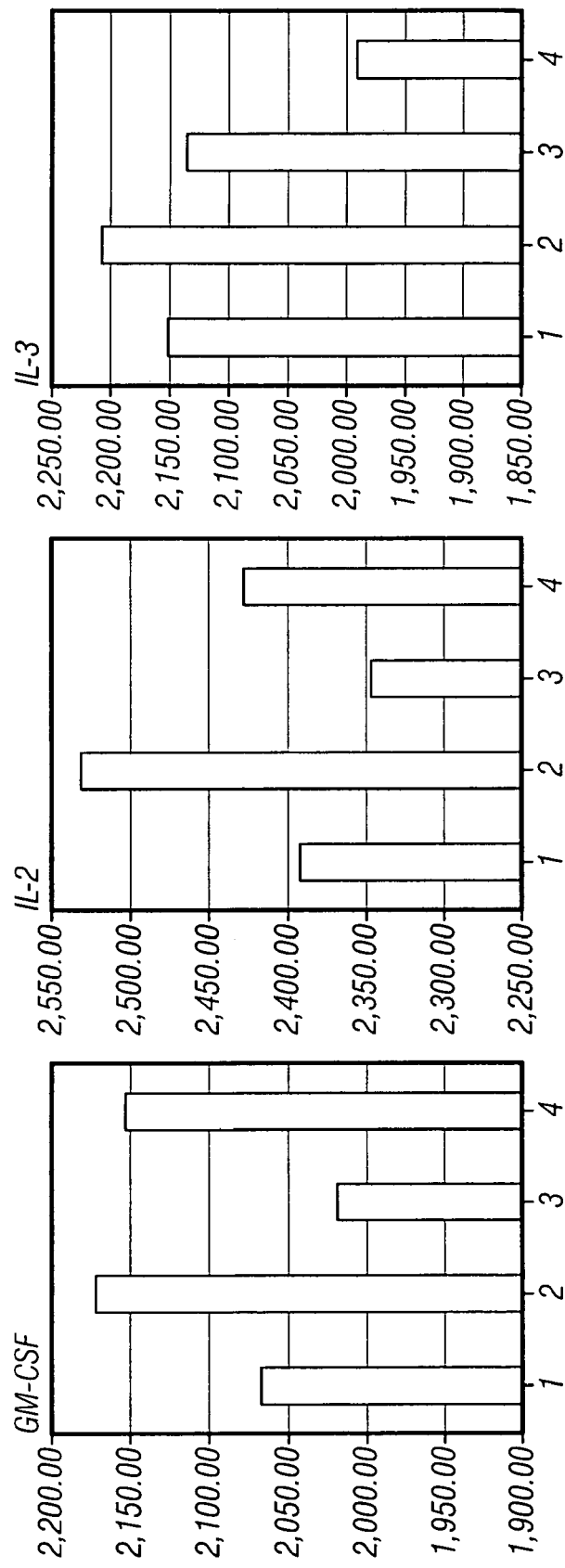
Figures 3, 4A:
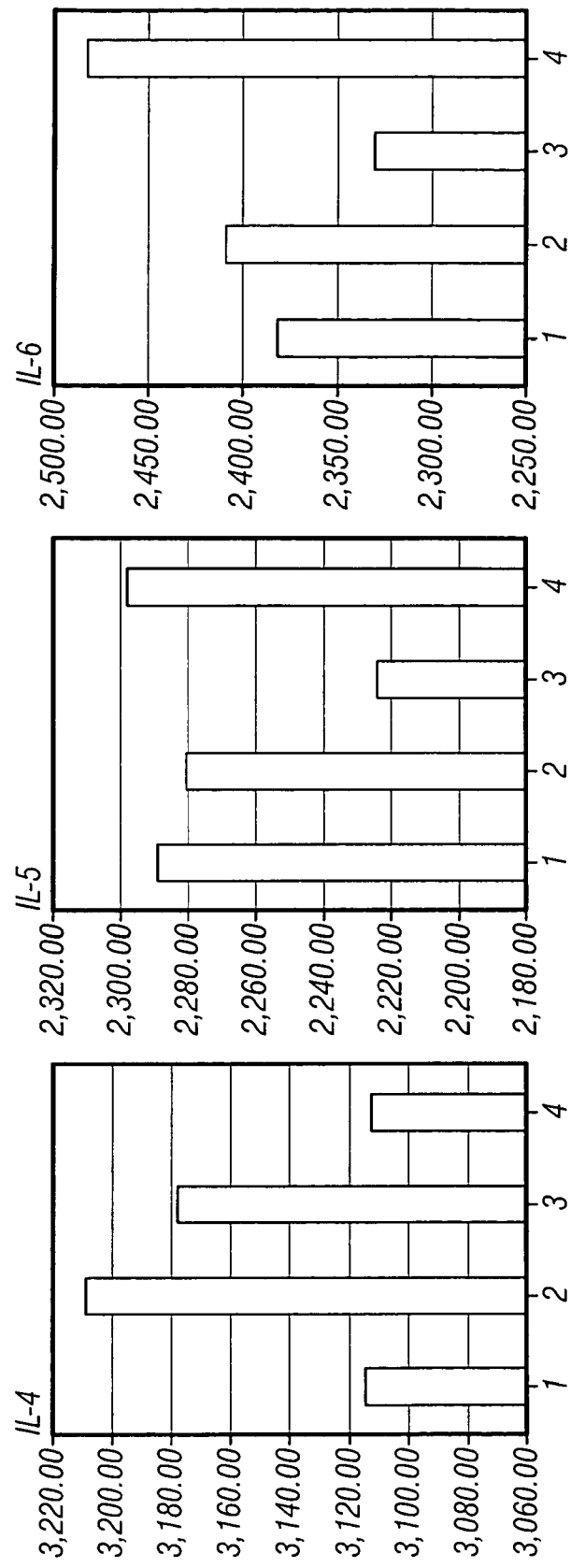
Figures 1, 4B:
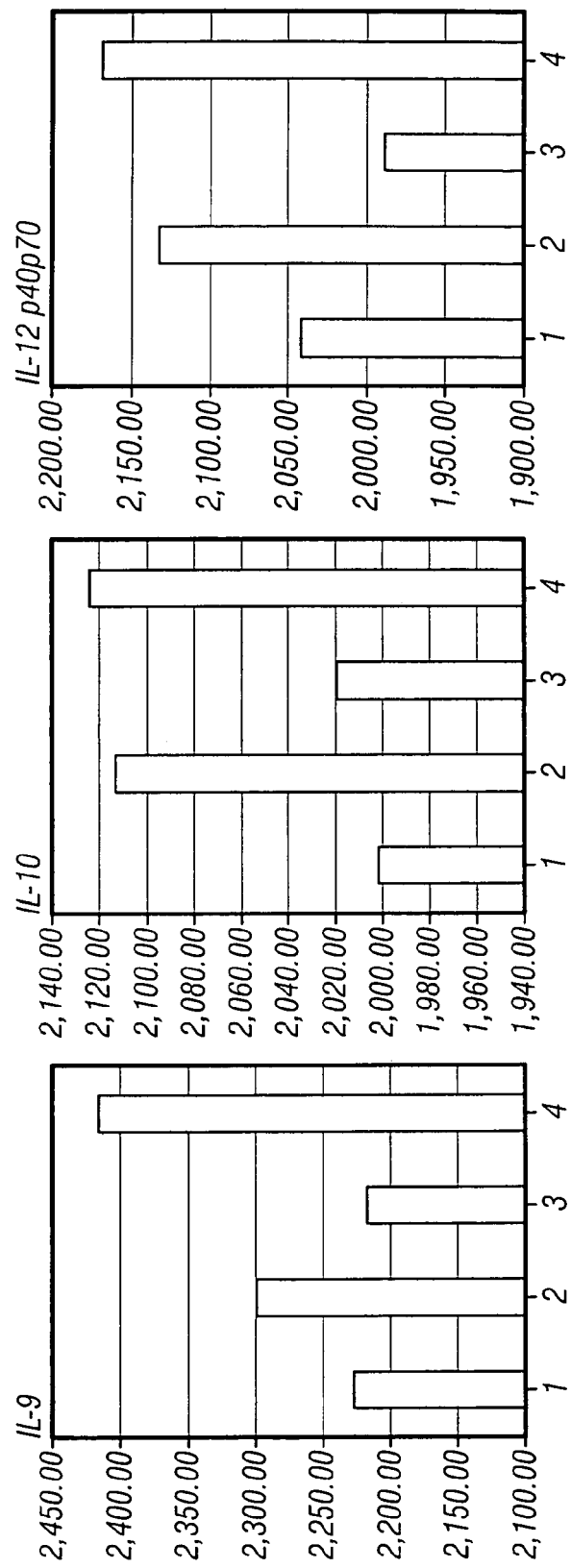
Figures 2, 4B:
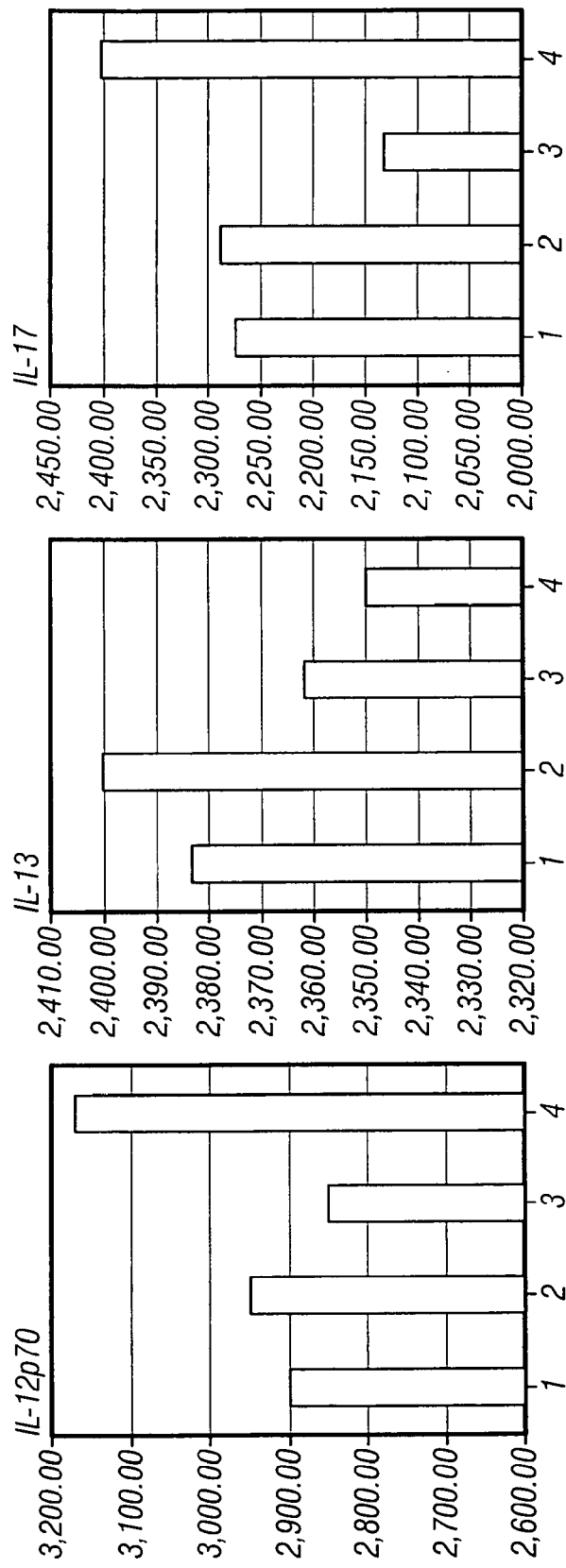
Figures 3, 4B:
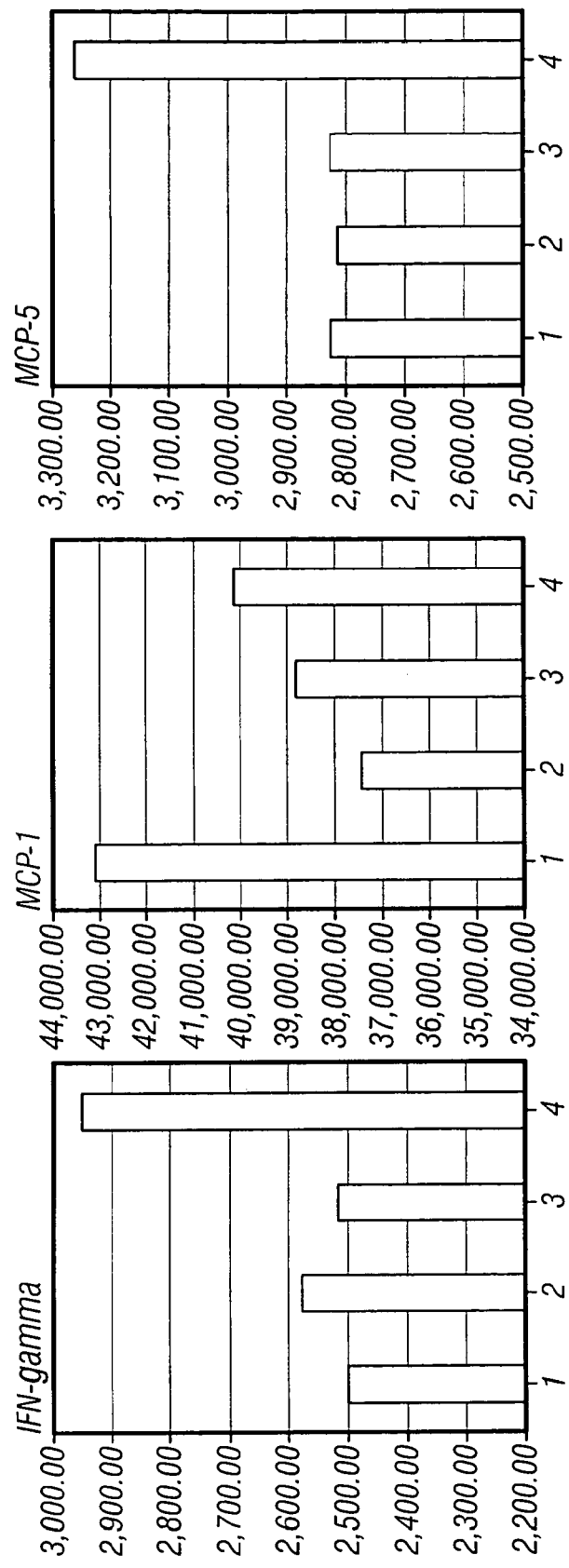
Figures 1, 4C:
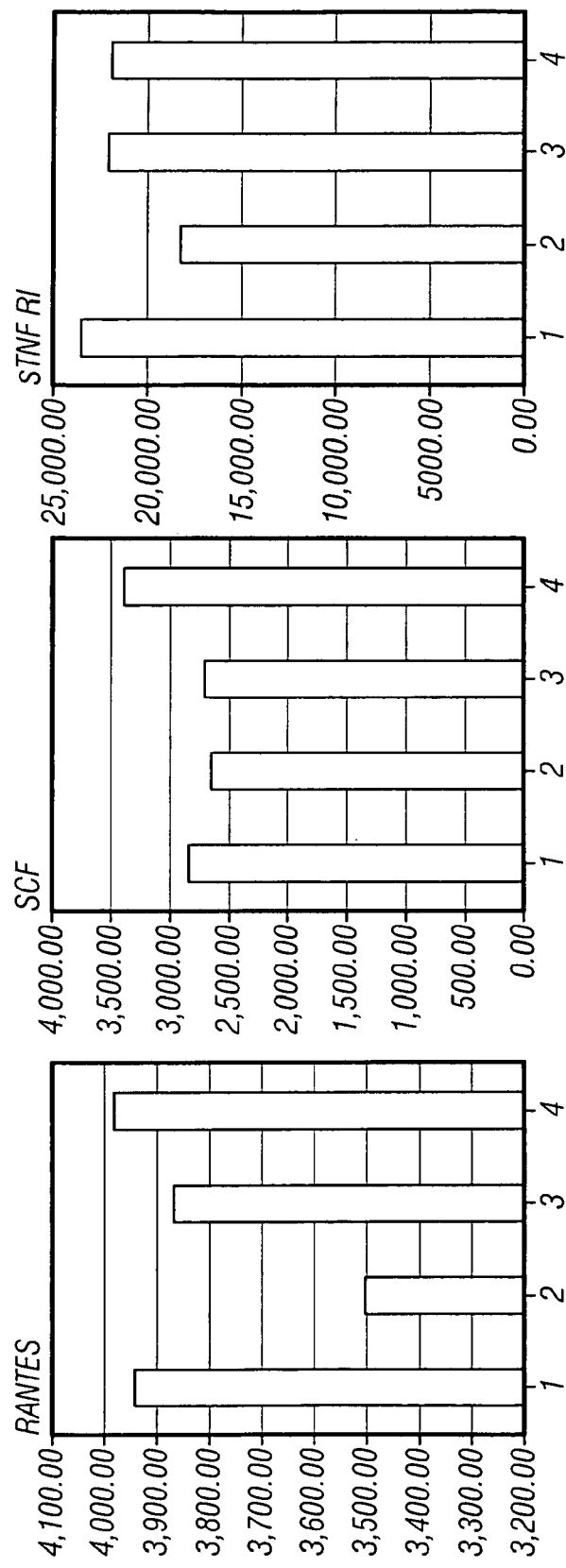
Figures 2, 4C:
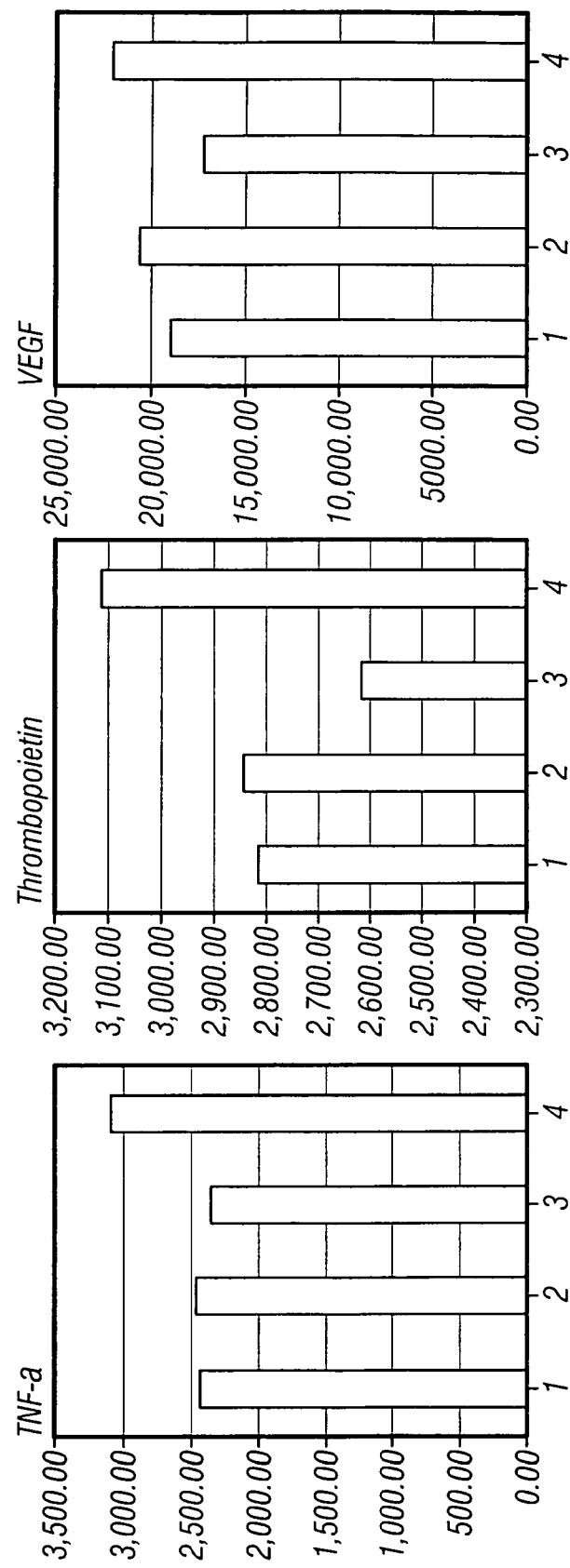

On each of the first four days post treatment, leukocyte counts were determined from nasal wash samples for each test animal and each control animal. The results of that testing is summarized in FIG. 1. FIG. 1 shows that leukocyte levels were lower in animals treated with TISF within the first four days, and it shows a statistical analysis of the data. The treated and control groups were compared using ANOVA, with the Bonferonni correction for multiple testing, using log-transformed total leukocyte counts per mL of nasal wash. Both the mean sum of leukocyte counts and the mean maximum leukocyte counts were lower in the treated subjects, and the differences were statistically significant for each measure of inflammation. See FIGS. 2 and 3. The lower leukocyte levels in the nasal wash from TISF treated subjects are indicative of less severe inflammation of the nasal passages in the treated animals.

EXAMPLE 2

Cells were stimulated with a solution containing 1 microgram of highly purified TISF. The cells were maintained for 24 hours post-treatment, at which time the supernatant was tested for cytokine levels using the RAYBIO® Mouse Cytokine Antibody Arrays I and 1.1 from RayBiotech. Both positive and negative controls were included in the test, and a background array was run as well: the background level of each cytokine has been subtracted from the data in FIG. 4. TISF stimulated production of at least IL-10, IL-12 (anti-inflammatory cytokines) and GM-CSF. It had no effect on TNF-α levels, and may have an inhibitory effect on MCP-1 (proinflammatory cytokine).

The cytokine level test was performed according to the User Manual provided by RayBiotech, Inc.

The foregoing detailed description of the invention and preferred embodiments, especially with respect to product compositions and processes, is to be considered illustrative of specific embodiments only. It is to be understood, however, that additional embodiments may be perceived by those skilled in the art. The embodiments described herein, together with those additional embodiments, are considered to be well within the scope of the present invention.

What is claimed is:

1. A method to reduce inflammation directly in a human, canine, ursine, bovine or ovine subject, comprising identifying a subject that exhibits inflammation due to a localized immune response not resulting from infection, administering to said subject an amount of T4 immune stimulating factor (TISF) effective to reduce the inflammation in a time period shorter than that required for an adaptive immune response, wherein said TISF is an isolated thymus-derived cationic protein factor expressed by a cloned type II thymic epithelial cell line of human, bovine, canine or feline origin, having a molecular weight of about 50,000 Daltons on a polyacrylamide gel, an isoelectric point of about 6.5, and capable of inducing or enhancing cell-mediated immune responsiveness of mature T-cells and stimulating IL-2 production in a mammal.

2. The method of claim 1, wherein the inflammation is inflammation of the subject's respiratory system.

3. The method of claim 1, wherein the inflammation is inflammation of the subject's upper respiratory system.

4. The method of claim 1, wherein the amount of TISF is administered by injection after the appearance of inflammation.

5. The method of claim 1, wherein the amount of TISF is administered orally.

6. The method of claim 1, wherein the amount of TISF is administered topically or by inhalation and is directed to a region where inflammation has developed.

7. The method of claim 1, wherein the inflammation is associated with an immunological disorder.

8. The method of claim 1, wherein the inflammation is associated with asthma or allergic rhinitis.

9. The method of claim 1, wherein the subject is a human.

10. The method of claim 1, wherein the subject is canine.

11. The method of claim 1, wherein the TISF is from a cell line of bovine origin.

* * * * *